(12) United States Patent
Bruce et al.

(10) Patent No.: US 9,821,542 B2
(45) Date of Patent: Nov. 21, 2017

(54) ELASTIC FILM LAMINATES PREPARED BY MULTIPLE STRETCHING STEPS

(75) Inventors: Stephen D. Bruce, Montpelier, VA (US); Jeffrey Alan Middlesworth, Wauconda, IL (US)

(73) Assignee: TREDGAR FILM PRODUCTS CORPORATION, Richmond, VA (US)

( * ) Notice: Subject to any disclaimer, the term of this patent is extended or adjusted under 35 U.S.C. 154(b) by 760 days.

(21) Appl. No.: 13/200,776

(22) Filed: Sep. 30, 2011

(65) Prior Publication Data

US 2012/0018083 A1 Jan. 26, 2012

Related U.S. Application Data

(62) Division of application No. 11/729,346, filed on Mar. 28, 2007, now abandoned.

(60) Provisional application No. 60/790,663, filed on Apr. 10, 2006.

(51) Int. Cl.
| | | |
|---|---|---|
| A61F 13/49 | (2006.01) |
| B32B 37/14 | (2006.01) |
| B32B 5/26 | (2006.01) |
| B32B 25/08 | (2006.01) |
| B32B 25/10 | (2006.01) |
| B32B 27/12 | (2006.01) |
| B32B 27/32 | (2006.01) |
| B32B 5/02 | (2006.01) |
| B32B 7/02 | (2006.01) |
| B32B 25/14 | (2006.01) |
| B32B 3/26 | (2006.01) |

(52) U.S. Cl.
CPC ........ *B32B 37/144* (2013.01); *A61F 13/4902* (2013.01); *B32B 3/266* (2013.01); *B32B 5/022* (2013.01); *B32B 5/26* (2013.01); *B32B 7/02* (2013.01); *B32B 25/08* (2013.01); *B32B 25/10* (2013.01); *B32B 25/14* (2013.01); *B32B 27/12* (2013.01); *B32B 27/32* (2013.01); *B32B 2305/20* (2013.01); *B32B 2307/51* (2013.01); *B32B 2307/724* (2013.01); *B32B 2307/726* (2013.01); *B32B 2555/02* (2013.01); *Y10T 428/24322* (2015.01); *Y10T 442/601* (2015.04); *Y10T 442/674* (2015.04)

(58) Field of Classification Search
CPC .......... A61F 13/49012; A61F 13/49014; A61F 13/49015; A61F 13/15593
USPC ................................ 156/160, 163, 164, 229
See application file for complete search history.

(56) References Cited

U.S. PATENT DOCUMENTS

| | | | | |
|---|---|---|---|---|
| 4,655,760 A | * | 4/1987 | Morman et al. ......... 604/385.26 |
| 4,720,415 A | * | 1/1988 | Vander Wielen et al. .... 428/152 |
| 5,143,679 A | | 9/1992 | Weber |
| (Continued) | | | | |

FOREIGN PATENT DOCUMENTS

| | | |
|---|---|---|
| JP | 2003-3118841 | 6/2003 |
| WO | WO-2007/061486 A1 * | 5/2007 |

*Primary Examiner* — Jeff Aftergut
(74) *Attorney, Agent, or Firm* — Karceski IP Law, PLLC; Jeffrey Karceski

(57) ABSTRACT

Elastic laminates and methods of making same are provided, wherein the laminate includes an elastic film laminated to at least one substrate web, and wherein the elastic film has been stretched at least twice prior to bonding the film to the substrate layer. Such laminates possess improved bond strength between the film and the substrate web and have greater elongation versus laminates made with a film that has been stretched only once.

20 Claims, 8 Drawing Sheets

(56) References Cited

U.S. PATENT DOCUMENTS

| | | | |
|---|---|---|---|
| 5,330,458 A | | 7/1994 | Buell |
| 5,344,691 A | * | 9/1994 | Hanschen et al. ............ 428/152 |
| 5,518,566 A | * | 5/1996 | Bridges et al. ............... 156/161 |
| 5,601,547 A | | 2/1997 | Kato |
| 5,620,780 A | | 4/1997 | Krueger |
| 5,733,628 A | | 3/1998 | Pelkie |
| 5,932,497 A | | 8/1999 | Morman |
| 6,159,584 A | | 12/2000 | Eaton |
| 6,255,236 B1 | * | 7/2001 | Cree et al. ................... 442/328 |
| 6,383,431 B1 | | 5/2002 | Dobrin |
| 6,413,249 B1 | * | 7/2002 | Turi et al. .................... 604/387 |
| 6,436,216 B1 | | 8/2002 | Grover |
| 8,007,484 B2 | * | 8/2011 | McCabe et al. ......... 604/385.27 |
| 2003/0022582 A1 | * | 1/2003 | Cree et al. ................... 442/394 |
| 2003/0181120 A1 | | 9/2003 | Wu |
| 2006/0003656 A1 | | 1/2006 | Morman |
| 2006/0003658 A1 | | 1/2006 | Hall |
| 2010/0285286 A1 | | 11/2010 | Middlesworth |

\* cited by examiner

ELASTIC FILM LAMINATES PREPARED BY MULTIPLE STRETCHING STEPS

CROSS-REFERENCE TO RELATED APPLICATIONS

This application is a divisional application of U.S. patent application Ser. No. 11/729,346, filed Mar. 28, 2007 entitled "Elastic Film Laminates Prepared by Multiple Stretching Steps", now abandoned, which claims the benefit of U.S. provisional Application No. 60/790,663, filed Apr. 10, 2006 and entitled "Elastic Film Laminates, Articles and Methods of Manufacturing Same".

FIELD OF THE DISCLOSURE

The disclosure relates to elastic film laminates, methods of manufacturing such laminates and articles incorporating same.

BACKGROUND OF THE DISCLOSURE

Elastic film laminates are used in the manufacture of many goods. In particular, elastic film laminates are used in the manufacture of absorbent articles, such as diapers, training pants adult incontinent articles, and similar articles. The elastic film laminates may be used, for example, as the waist band, leg cuffs, side tabs, side ears, side panels or as the shell of the article. Elastic film laminates also find use in other articles, such as garments, hats, gowns, coveralls, etc. and are typically used to provide desired fit characteristics to the article.

When a film or laminate is made in roll form, the material travels along a path known as the machine direction ("MD") beginning where the material is formed or unwound to the point where the finished web is wound on a roll. The machine direction will normally correspond to the longest dimension of the web. The cross direction ("CD") is a direction generally perpendicular to the machine direction and will typically correspond to the width of the web. A number of elastic films and laminates have been proposed, but the vast majority of such films and laminates are engineered and constructed to provide stretch in the cross direction ("CD").

Heretofore, the most common form of elastic laminate having stretch in the machine direction have not used film, but instead have employed a laminate of elastic strands, such as strands of LYCRA® brand elastomer. In the manufacture of elastic strand laminates, the strands are placed under tension and adhesively laminated to at least one, and typically two nonwoven fibrous webs. The nonwoven webs provide a cloth like texture to the laminate which is preferred by the consumer, as is known. The elastic strands are then allowed to relax, causing the nonwoven to gather and pucker, resulting in a bulky appearance. In some applications, such as training pants and adult incontinent articles, the bulky appearance is objectionable. In order to make the resulting laminate smoother and less bulky, the number of elastic strands used needs to be increased approximately three-fold. The increased number of elastic strands adds to the cost of the laminate, and also results in significantly more complicated and less robust manufacturing process. The increased number of strands becomes difficult to manage and, if any of the strands would break, the process needs to be stopped for a considerable period of time while the strand(s) are re-threaded into the machine.

Accordingly, there is a need for a smoother, less bulky elastic film laminate that has improved properties and can be manufactured in a robust process.

SUMMARY OF THE DISCLOSURE

In one embodiment, the invention provides a method of making an elastic film laminate, the method comprises stretching the film in multiple steps prior to laminating the film to at least one substrate.

In another embodiment, the invention provides an elastic film laminate comprising an elastic film bonded to at least one substrate, wherein the film has been stretched in multiple steps prior to being bonded to the substrate.

In yet another embodiment, the invention provides an article of clothing comprising an elastic film laminate, wherein the film laminate comprises an elastic film bonded to at least one substrate, wherein the film has been stretched in multiple steps prior to being bonded to the substrate.

These and other aspects of the invention will become apparent upon a further reading of the specification with reference to the drawing figures and the appended claims.

DETAILED DESCRIPTION OF THE EMBODIMENTS

Figure 1:
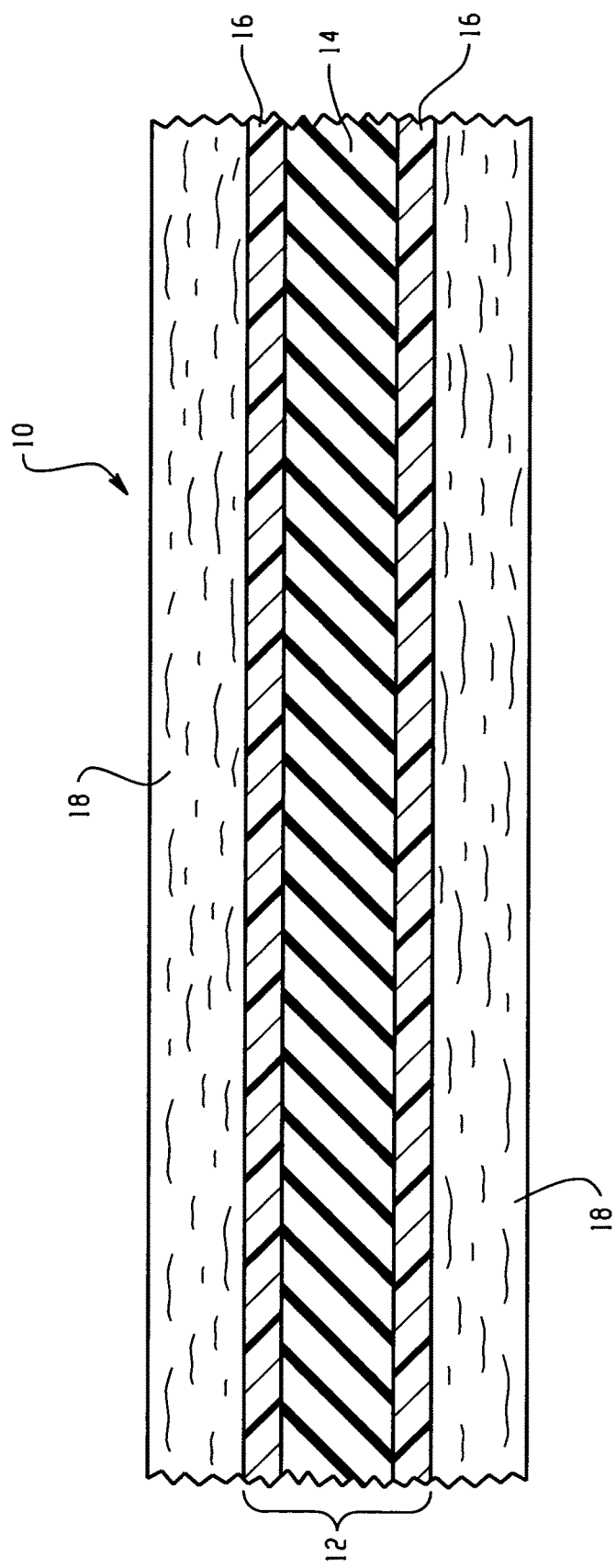
FIG. 1 is a schematic diagram outlining the steps in an exemplary process of making an elastic film laminate according to the invention.

With reference first being made to FIG. 1, illustrated therein is one embodiment of an elastic film laminate in accordance with the invention. As used herein, the term "elastic film laminate" connotes a structure comprising an elastic film bonded to at least one substrate. The elastic film laminate 10 shown in FIG. 1 comprises an elastic film 12 having an elastomeric core 14. Preferably the film 12 further comprises at least one skin layer 16 disposed on at least one side of the elastomeric core 14. Most preferably, the core 14 will have at least one skin layer 16 on each side thereof, as illustrated in FIG. 1. It is to be understood that embodiments having more then one skin layer on each side of the elastic core 14 are also contemplated and may be used to advantage. Attached to the elastic film 12 is at least one substrate, such as nonwoven web 18. In a preferred embodiment, the laminate will comprise a nonwoven web 18 attached to each side of the elastic film 12.

As noted, the elastic film 12 comprises an elastic core 14 and, optionally, one or more skin layers 16. The elastomeric core 14 comprises natural or synthetic rubbers, such as isoprenes, butadiene-styrene materials, styrene block copolymers (e.g., styrene/isoprene/styrene (SIS), styrene/butadiene/styrene (SBS), or styrene/ethylene-butadiene/styrene (SEBS) block copolymers) olefinic elastomers, polyetheresters, polyurethanes, for example, and mixtures thereof.

If one or more skin layers 16 are to be used with elastic core 14, it is preferable that the elastic film 12 be made in a co-extrusion process, in which the elastic core 14 and the one or more skin layers 16 are extruded simultaneously from a die. Alternatively, processes such as extrusion coating could be used to produce the multilayer film 12. The skin layers 16, if used, can comprise any suitable material that is less elastic than the elastic core 14. Preferred materials are polyolefin polymers, specifically polyethylene polymers and copolymers, including metallocene-catalyzed polyethylene and blends of polyethylene polymers or copolymers. Other materials, such as vinyl acetate copolymers, may also be used to advantage if desired.

The relative amounts of skin layer 16 to core layer 14 in the elastic film 12 can vary depending on the particular application and the desired properties. Preferred embodiments for a multilayer elastic film 12 range from 5/90/5 to 15/70/15 by weight of skin/core/skin. The elastic film 12 may be embossed using a textured roller, as is known in the art, or may be made with a smooth surface. For example, a vacuum box may be employed to advantage to make a film with a smooth surface. The vacuum box imparts a partial vacuum to the elastic film 12 during the manufacturing process, drawing the film against a cast roll, producing a film that is smoother and generally of a thinner gauge than those produced without a vacuum box.

The nonwoven webs 18 may be bonded to the elastic film 12 in any suitable manner, such as, for example, by adhesive bonding, ultrasonic bonding, thermal bonding, point bonding, or other suitable method. Combinations of bonding methods may also be employed.

The term "nonwoven web" connotes a web of fibers interlaced and intertangled, but not in any regular or repeating pattern. Nonwoven fibrous webs are well known in the art and widely available. Such webs can comprise spunbonded, meltblown or carded webs, for example and can be monofilament fibers or bi-component fibers having a core-sheath structure. The nonwoven web 18 may be extensible, inextensible, elastic or inelastic. The term "elastic" is used to connote a material that can be stretched in at least one direction to approximately 150% of its original dimension and, when the tension is released, will return to a dimension that is no greater than 125% of its original dimension. For example, a material that is one inch long is elastic if it can be stretched to 1.5 inches in length and will return to be no more than 1.25 inches when the tension is released and the material is allowed to relax.

Figure 2:
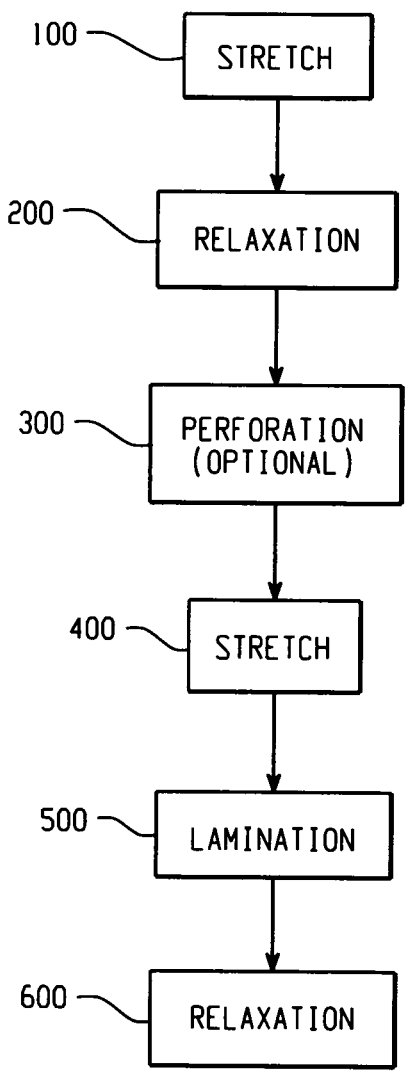
FIG. 2 is a schematic illustration of an elastic film laminate in accordance with the invention.

With reference now being made to FIG. 2, a schematic diagram of an exemplary process for making a laminate in accordance with the invention is depicted. After the elastic film 12 is formed, it undergoes a first stretching step 100. In the first or initial stretching step 100, the elastic film 12 is elongated or stretched in an amount sufficient to reduce the recovery force of the film. The amount of stretch necessary to accomplish this end point will vary with the type of elastomer used, the specific construction of the film, the basis weight of the film, and similar considerations. In preferred embodiments, the film is stretched to 400% or more in the initial stretching step 100. In particularly preferred embodiments, the film is stretched in the machine direction, although it could be stretched in the cross direction in lieu of or in addition to stretching in the machine direction.

The stretching in step 100 can be accomplished by any known and suitable stretching process and apparatus. For example, the film can be run through two sets of spaced-apart rollers, with the downstream pair of rollers operating at a higher rate of speed than the upstream pair to elongate the film in the MD. Alternatively, the film could be subjected to a tenter frame to orient the film in the CD if so desired. Or the film could be subjected to an intermeshing gear ("IMG") stretching operation in which the film is forced through a nip formed by two complimentary toothed rollers in a mating relationship. As the film passes through the nip formed by the intermeshing teeth or the rollers, it elongates and is stretched. IMG stretching can be accomplished in either the MD or CD as desired. Other stretching operations known in the art, or combinations of stretching methods, may also be used to advantage. If skins 16 are present in the elastic film 12, the stretching step 100 will be sufficient to deform the skins and thus permit the elastic core to elongate and retract, as is known in the art.

After the film is stretched in the initial stretching step 100, the film 12 is allowed to relax during the relaxation step 200. At this point, the film is generally not under any appreciable tension, except that necessary to carry the film in the MD and to support the film during any processing that might take place prior to the next stretching operation. For example, while the film is relaxed during this step, it is advantageous to process the film to impart breathability, if desired, at the optional perforation step 300.

Processes to impart breathability include perforation, slitting and other techniques, such as hot needle perforation, die cutting, scoring, shearing, or through the use of high pressure water jets. Combinations of such methods may also be employed. Applicants have discovered that the film 12 is less prone to tearing or breaking if the perforations are added after the initial stretching step 100 as compared to perforating the film before the first stretching step. The perforations or slits, if used, may be introduced selectively, that is, only in pre-determined areas of the film 12. The number, size and shape of the perforations will be determined by the particular desired properties of the finished laminate. The perforations may also permit better handling of the film with a "cut-and-place" apparatus, as more fully described below.

Although not particularly preferred, breathability can be imparted by using a vacuum forming process in making the elastic film 12. Such an embodiment is not preferred because the film has a greater tendency to tear, rip or break during stretching if apertured before the first stretching step 100. Similarly, breathability may be imparted to the film 12 subsequent to the second stretching step 400, if desired.

Subsequent to the relaxation step 200 and any optional perforation of the film, the film 12 is again stretched during stretching step 400. As with first stretching step 100, the process or apparatus used to stretch the film 12 is not material to the invention. The degree of stretch during step 400 is equal to or less than the amount of stretch imparted during the first stretching step 100. In preferred embodiments, the degree of stretch during the second stretching step 400 is less than that imparted in first stretching step 100. For example, if the film 12 is stretched by 300% (equivalent to a 4:1 draw ratio) during the first stretch step 100, it may be stretched by 210% (3.1:1 draw ratio) during the second stretch step 400. Similarly, if the film 12 is stretched 400%

(5:1 draw ratio) during the first stretch step 100, it may be stretched no more than 350% (4.5:1 draw ratio) during the second stretching step 400.

Because the film has been pre-stretched during step 100, the force needed to stretch the film a second time will decrease, and may decrease by up to 80%. In addition, the first stretching step 100 results in the film having reduced recovery forces, that is, the force exerted by the film as it tries to resume its original dimension. Thus, less force is required to maintain the film under tension during second stretching step 400.

It should be noted that the process depicted in FIG. 2 shows only two stretching steps, which is the minimum number of stretching steps in accordance with the invention. However, more than two stretching steps may be employed if desired.

While the film is still in a stretched condition during second (or subsequent) stretching step 400, it may advantageously be attached to the nonwoven web(s) 18 if desired during the lamination step 500. Bonding the nonwoven(s) to the film while the film is stretched will result in the nonwoven webs being gathered when the tension on the film is released. The laminate will then be able to extend at least to the point that the film was stretched at the time of bonding to the nonwoven, without destroying or disrupting the bonds or deforming the fibers in the nonwoven web.

Applicants have discovered that the process of the invention results in improved bond strength between the film and the nonwoven web(s). While not intending to be bound by any particular theory, Applicants believe that the lower recovery forces in the elastic film reduces the forces that the film exerts in trying to pull away from the nonwoven web(s), resulting in a stronger bond.

During the lamination step 500, the film 12 is laminated to one or more nonwoven web(s) 18. The lamination may be accomplished using any suitable technique, such as, for instance, adhesive lamination, thermal bonding, ultrasonic bonding, pressure bonding or dynamic mechanical bonding. Combinations of such techniques may also be employed to advantage.

Following the lamination step 500, the resulting laminate 10 is allowed to relax during relaxation step 600. Surprisingly, the laminate formed by a multiple stretch process has greater elongation than a laminate made using a single stretch process.

The lower recovery forces (which can also be viewed as the force necessary to hold the film in a stretch condition) following relaxation step 200 can also be advantageous when the film is being used in a cut-and-place type apparatus. Cut-and-place type apparatus are used in many diaper manufacturing operations and in other industrial processes. These apparatus typically use a vacuum pressure to maintain a material in place while the material is cut into a desired size or shape, and then place or move the cut piece of material to another location in the process.

In the context of the present invention, a cut-and-place apparatus may be used in a diaper manufacturing operation to form, for example, a side ear or side panel for a diaper. Specifically, the elastic film 12 may undergo a first stretching operation 100, relaxation step 200 and optional perforation step 300 at the location of manufacture. The material may then be wound on a roll and sent to the diaper manufacturer, where the film is unwound and undergoes the second stretch operation 400. While the film is under tension during stretching step 400, it is brought into contact with the vacuum device and is cut to the desired size and shape. As soon as the material is cut, the only force holding it under tension is the vacuum pressure. At this point, the cut piece of film is laminated to the nonwoven web(s) and the lamination step 500, whereupon it is released from the vacuum. At this point the elastic film is still held under tension by the nonwoven web and if another nonwoven web is to be laminated, is maintained under tension until the second nonwoven web is attached, after which it is allowed to relax at step 600.

It is apparent from this description that the recovery forces of the elastic film need to be matched to the ability of the cut-and-place apparatus to retain the material under tension. Apart from the recovery forces, such factors as coefficient of friction need to be considered. However, all things being equal, pre-stretching the elastic film in accordance with the invention provides a convenient, cost-effective solution without having to reduce the basis weight of the film, add tackifiers to the skin layers (which can be detrimental to film handling concerns) or take other measures.

Although the embodiments discussed reference bonding the elastic film to one or more nonwoven web(s), it is understood that other substrates may be used if desired. Examples of suitable substrates include thermoplastic film material, such as polyethylene, polypropylene, ethylene vinyl acetate and other such polymeric materials; fibrous material (which can comprise a fibrous web, woven and/or non-woven materials, including polyesters, polyolefins, acrylics, rayons, cottons and other cellulose materials, thermoplastic elastomers, and blends of the same, etc.).

The embodiments described in detail contemplate that the film 12 is stretched relatively uniformly along its length, width or both. However, it is understood that certain embodiments may provide for the film to be stretched intermittently or only in certain areas, to provide for desired laminate properties. For example, IMG stretching is one form of intermittent stretching because the points where the film contacts the teeth of the rollers act as grip points. The film does not stretch at the grip points, but does stretch at locations immediately adjacent to the grip points. As the depth of IMG activation increases, the length of the stretched area increases until the entire region of the film located between the teeth is stretched.

Figure 3:
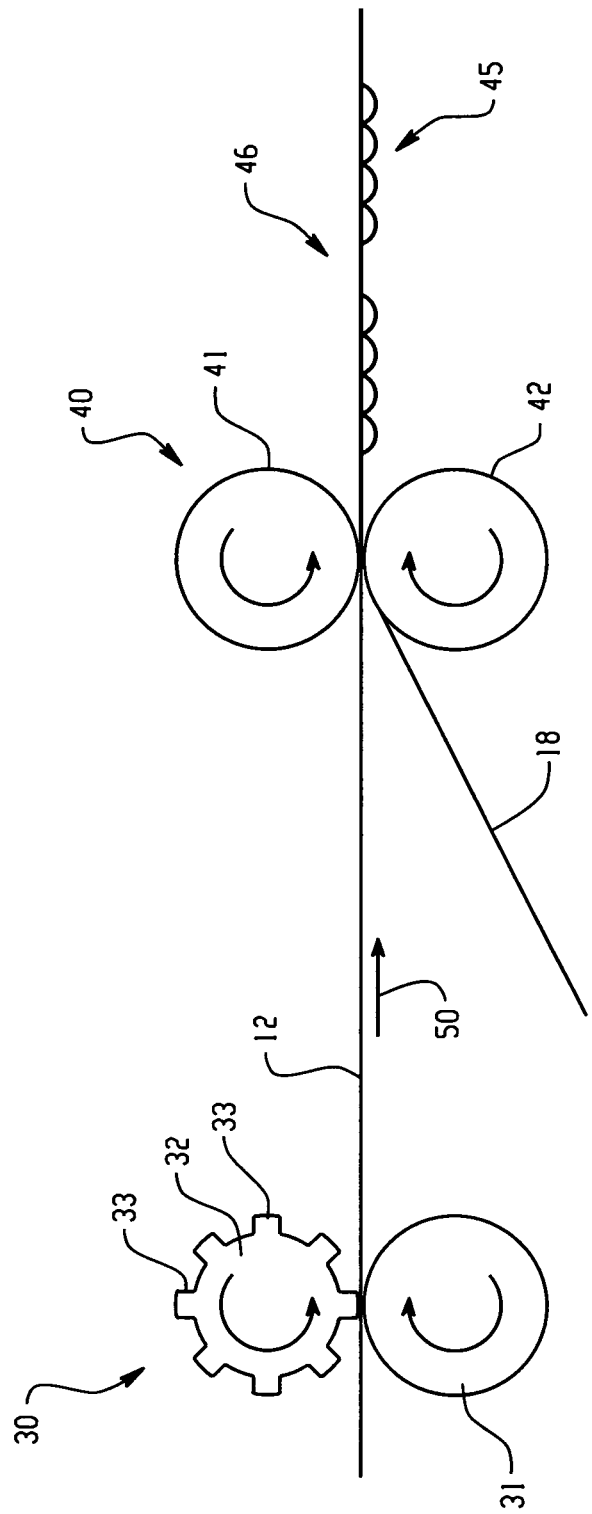
FIG. 3 is a schematic illustration of an intermittent stretching process that may be used in the invention.

Another example of intermittent stretching is illustrated in FIG. 3 and comprises the use of two nips, the first nip 30 formed of a smooth roller 31 and a ribbed roller 32 and the second nip 40 formed of two smooth rollers 41, 42. The ribbed roller has parallel, raised sections or ribs 33 that run the length of the roller (i.e., into and out of the plane of the paper as seen in FIG. 3). As the roller rotates, the film 12 is alternately gripped by the raised ribs 33 and released. The rollers 41, 42 of second nip 40 are rotating at a faster rate of speed than the rollers of the first nip. In the embodiment shown in FIG. 3, the film 12 is moving in the direction from nip 30 toward nip 40, as seen by arrow 50. Thus, as the film 12 is alternately gripped and released by the first nip, the film is intermittently stretched and not stretched. Stretching of film 12 occurs in the region between the first nip 30 and the second nip 40. The speed of rotation of ribbed roller 32, as well as the number of ribs 33, the size and shape of the ribs 33, and the spacing between adjacent ribs 33 on the roller 32 will determine the relative size of the stretched and non-stretched areas. The relative speed of the rollers 41, 42 of the second nip 40 will determine the degree of stretch imparted to the film 12.

As also seen in FIG. 3, substrate 18 may be introduced at the second nip roller whereby substrate 18 will be laminated to the film 12. The resulting laminate will comprise extensible regions 45 separated by inextensible regions 46 as seen in FIG. 3. the extensible regions will correspond to the locations where the film 12 was under tension while bonded to the substrate 18 and the inextensible regions 46 will correspond to the locations where the substrate 18 was laminated to film 12 while film 12 was not under tension.

It is contemplated that the ribs 33 may correspond to the width of the film 12, or may be wider or narrower than the film 12. If narrower than the width of the film 12, then the film will only be gripped in a portion along its width corresponding to the location of the ribs 33. Such embodiments can provide even greater variation in the properties of the laminate. In addition, it is contemplated that alternate methods of intermittently gripping and releasing the film may be used in lieu of the ribbed roller 32. For example, both rollers of nip 30 could be smooth and one such roller moved into and out of engagement with the film 112 by use of a rotating cam or other actuator device.

EXAMPLES

Table 1 illustrates the reduction in force needed to elongate the films between the first and second stretching steps for two films that were identical, except for the difference in basis weight. Because the films require less force to elongate after the first stretch, they also require less force to hold the film in a stretched condition (i.e., they have a reduced recovery force as well).

In the examples, two films were prepared, one having a basis weight of 30 grams/sq. meter ("gsm") and the other having a basis weight of 40 gsm. The films were first stretched to 400% elongation (reported as the "Pre-Strain" in Table 1) and relaxed. Then the films were stretched to 300% elongation in a second stretching step (reported as "First Cycle" in the table). The force necessary to stretch the films is reported in Table 1.

TABLE 1

| Basis weight | Pre-Strain (400%) | First Cycle (300%) | Force Reduction |
|---|---|---|---|
| 30 gsm | 1676 grams | 930 grams | 44.5% |
| 40 gsm | 2200 grams | 1331 grams | 39.5% |

Figure 4:
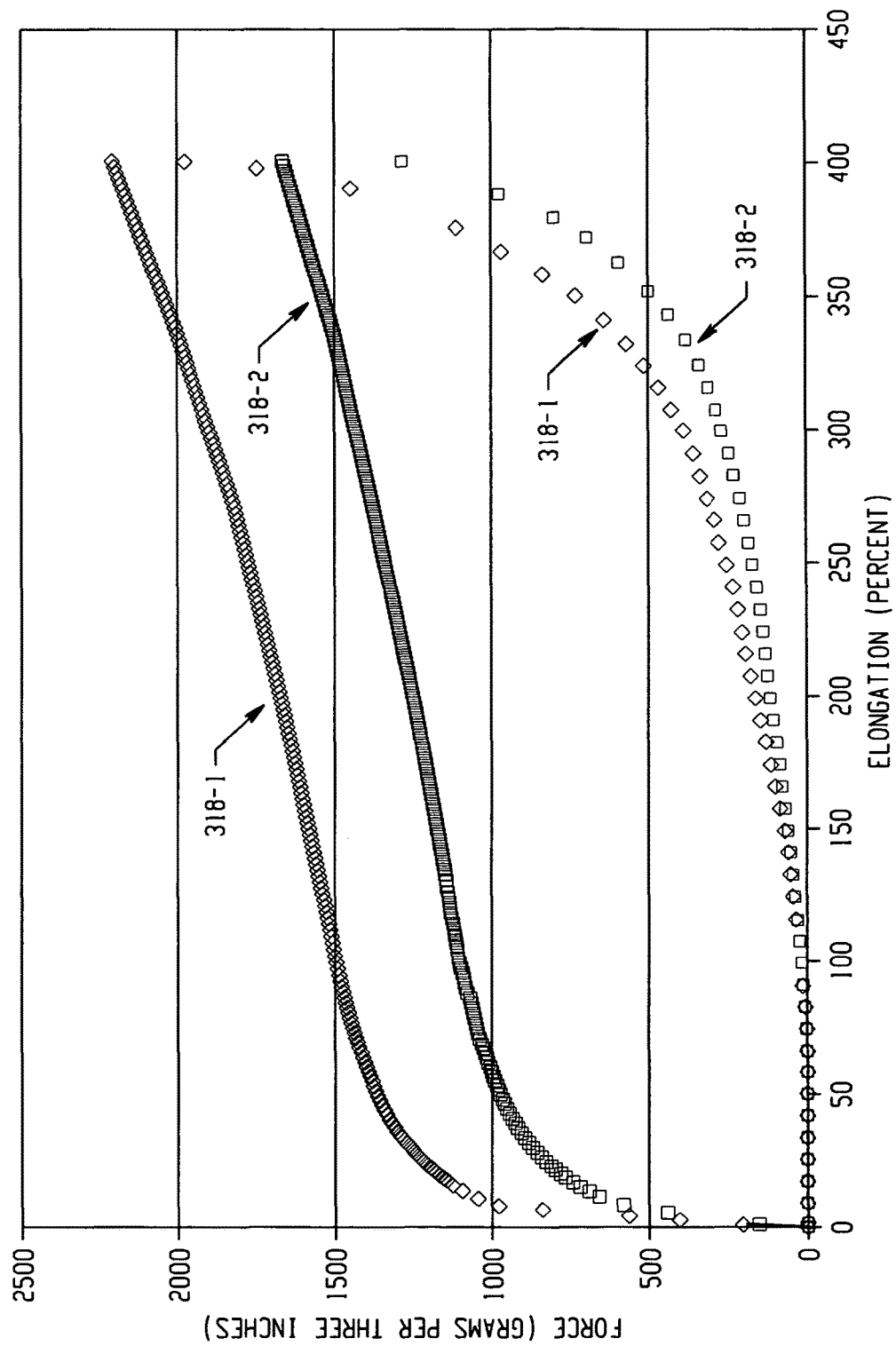
FIG. 4 is a graph plotting percent elongation versus force of a first stretch cycle of an embodiment.
Figure 5:
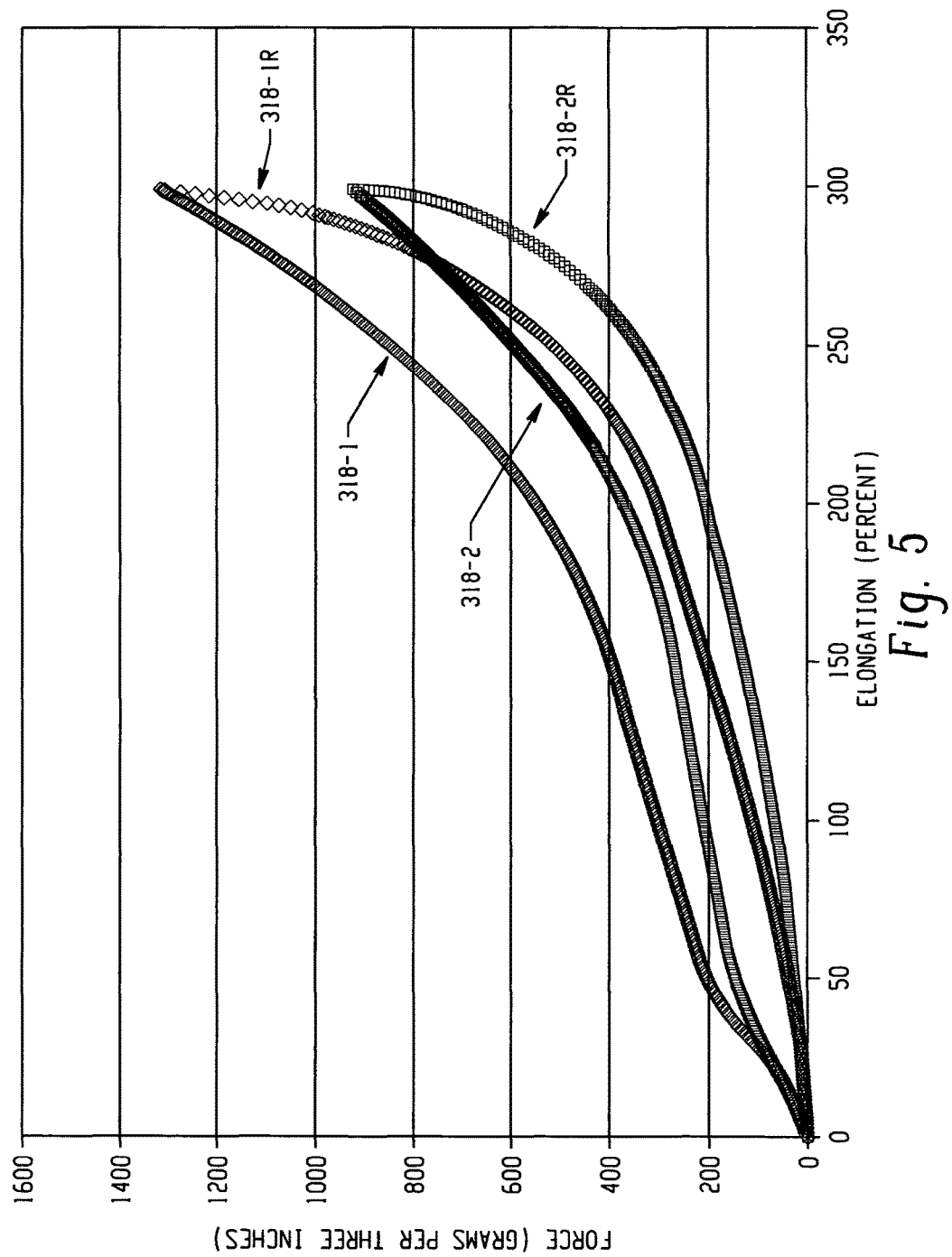
FIG. 5 is a graph plotting percent elongation versus force of a second stretch cycle of an embodiment.

FIGS. 4-8 plot the data of force versus percentage elongation. Specifically, FIG. 4 shows the force required to initially stretch ("Pre-Strain") the 30 gsm and 40 gsm films to 400% elongation. The curve corresponding to the 40 gsm film is curve 318-1 and the curve representing the 30 gsm film is 318-2. The recovery curves are also shown and labeled as 318-1R and 318-2R, respectively. FIG. 5 shows a similar graph for the second stretch step ("First Cycle") of the films. The same numbers were used to identify the samples.

Figure 6:
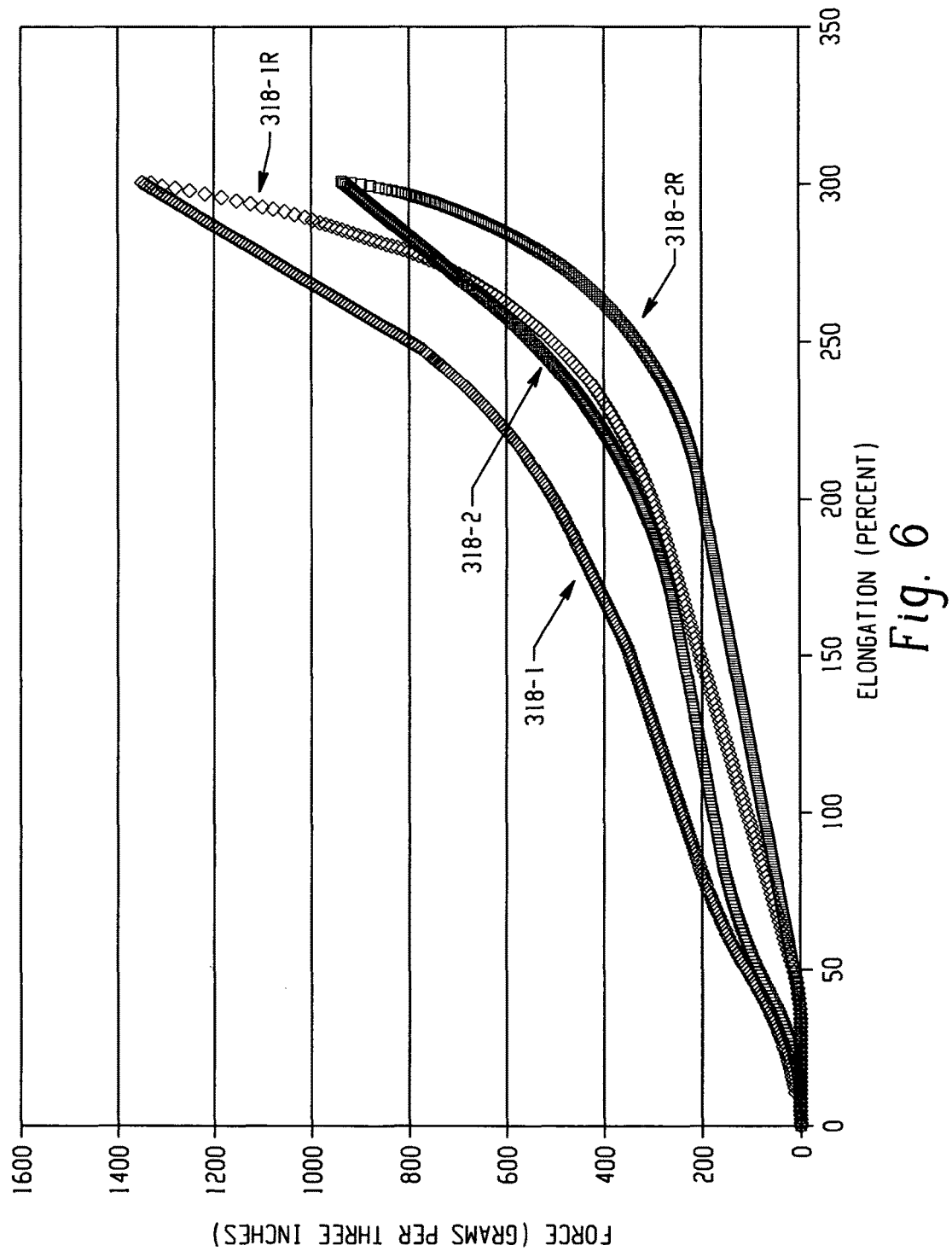
FIG. 6 is a graph plotting percent elongation versus force of a third stretch cycle of an embodiment.
Figure 7:
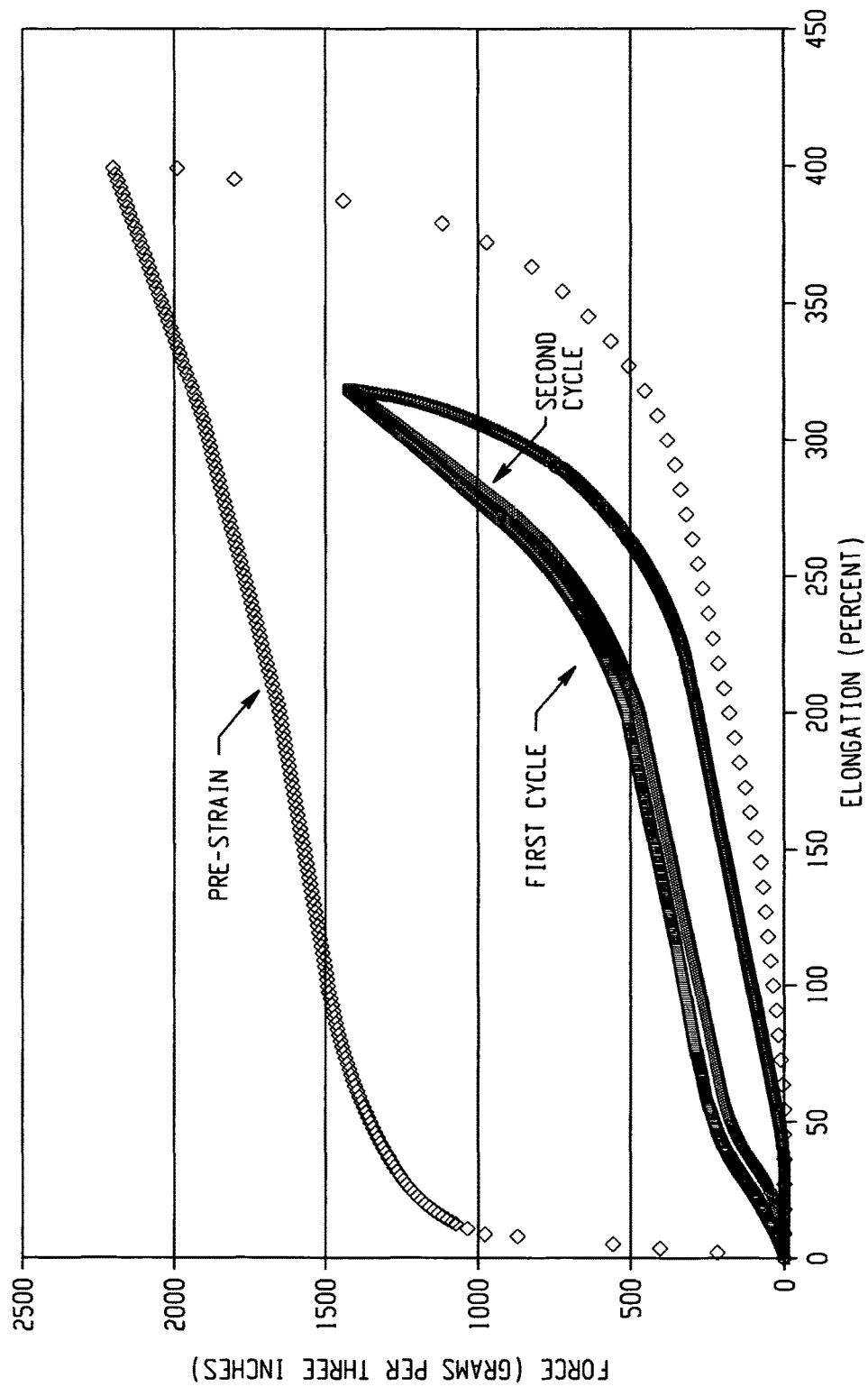
FIG. 7 is a composite graph plotting percent elongation versus force for three stretch cycles of an embodiment having a basis weight of 40 gsm.
Figure 8:
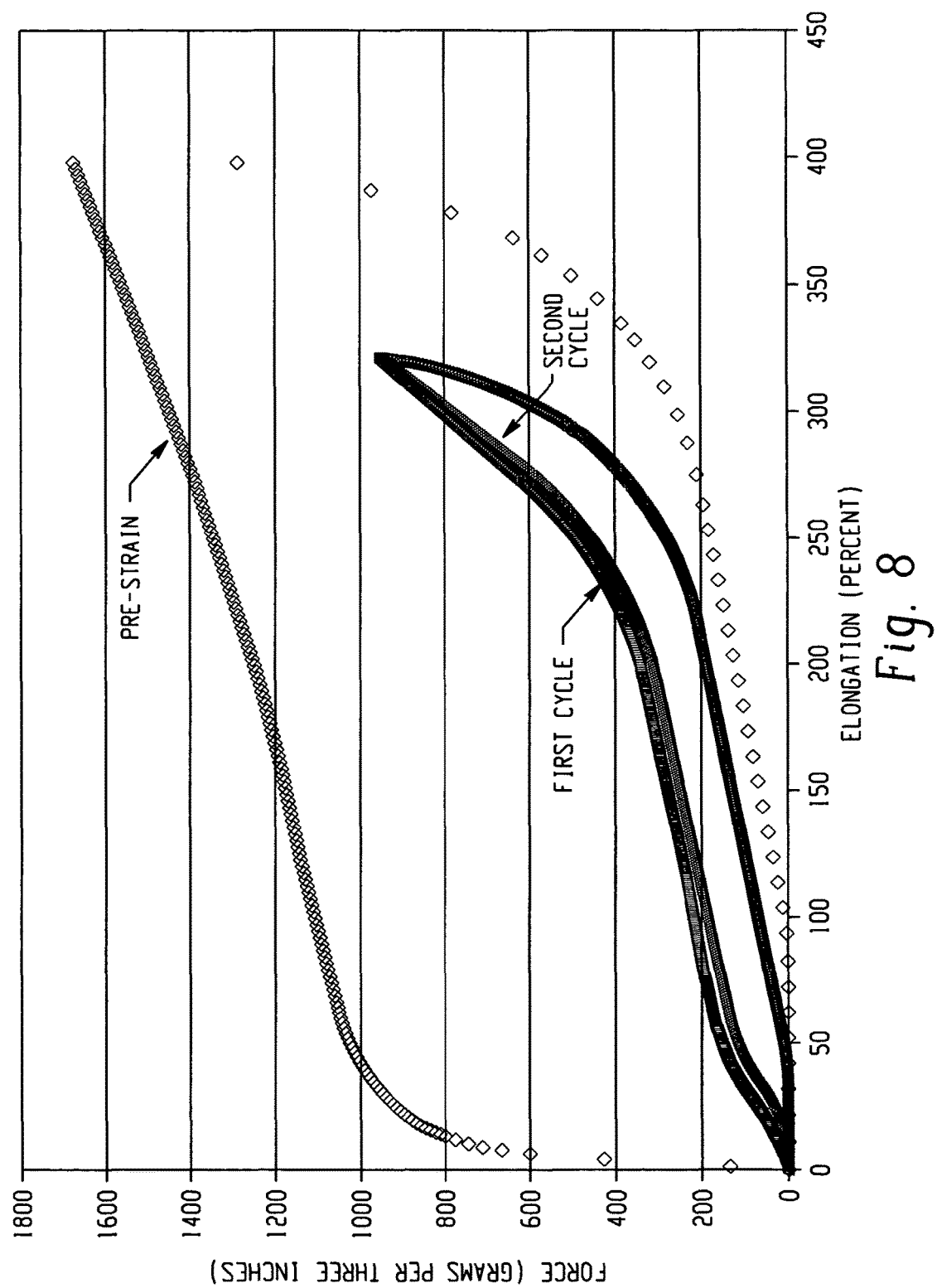
FIG. 8 is a composite graph plotting percent elongation versus force for three stretch cycles an embodiment having a basis weight of 30 gsm.

FIG. 6 is a similar graph showing the force necessary to elongate the films to 300% in a third stretching step. As best seen in FIGS. 7 and 8, (which are composite graphs of FIGS. 4-6 for the 40 gsm film and the 30 gsm film, respectively), a significant difference is seen between the force needed to initially stretch the films as compared to the second stretching, yet very little difference in force is required to stretch the film a third of subsequent times.

Although the present invention has been described with respect to various specific embodiments, various modifications will be apparent from the present disclosure and are intended to be within the scope of the following claims.

We claim:

1. A process of manufacturing a laminate, the process comprising:
    providing an elastic film comprising a styrene/isoprene/styrene core and one or more skin layers of a polyethylene polymer;
    stretching the film in the machine direction to a 4:1 draw ratio or greater in a first stretching step;
    relaxing the film after the first stretching step;
    perforating the film after relaxing the film;
    stretching the film at least once more in the machine direction less than the draw ratio after perforating the film in a second stretching step such that the film is stretched less in the second stretching step than in the first stretching step;
    laminating the film to at least one substrate web while the film is stretched in the second stretching step to form a laminate; and
    relaxing the laminate.

2. The process of claim 1, wherein the second stretching step comprises laminating the film to at least one nonwoven web.

3. The process of claim 1, wherein the elastic film comprises an elastic core and at least one skin layer.

4. The process of claim 3, wherein providing the elastic film comprises co-extruding an elastic film having an elastic core and at least two skin layers.

5. The process of claim 1, wherein providing the elastic film, stretching the film in the first stretching step, relaxing the film after the first stretching step and perforating the film after relaxation are performed by a film manufacturer when stretching the film in the second stretching step, laminating the film, and relaxing the laminate are performed by an article manufacturer.

6. The process of claim 5, wherein at least a portion of stretching the film in the second stretching step, laminating the film, or relaxing the laminate involve the use of a cut-and-place apparatus.

7. The process of claim 1, further comprising:
    winding the film after perforation; and
    unwinding the film prior to the second stretching step.

8. The process of claim 1, wherein at least one of the following: stretching the film in the first stretching step or stretching the film in the second stretching step comprises intermittently stretching the film.

9. The process of claim 8, wherein stretching the film in the first stretching step comprises intermittently stretching the film.

10. The process of claim 9, wherein the film is intermittently stretched using intermeshing gear stretching.

11. The process of claim 8, wherein stretching the film in the second stretching step comprises intermittently stretching the film.

12. The process of claim 8, wherein the film is intermittently stretched in a machine direction using intermeshing gear stretching in the first stretching step and wherein the intermittent stretching in the second stretching step comprises alternately gripping the film with a ribbed roller such that the film is alternately placed under tension in the machine direction and stretched between the ribbed roller and a downstream nip operating at a greater rotation speed as compared to the ribbed roller.

13. A process of manufacturing a laminate, the process comprising: providing an elastic film comprising a styrene/isoprene/styrene core and one or more skin layers of a polyethylene polymer;

intermittently stretching the film in the machine direction to a 4:1 draw ratio or greater in a first stretching step;

relaxing the film after the first stretching step;

perforating the film after relaxing the film;

intermittently stretching the film at least once more in the machine direction less than the draw ratio after perforating the film in a second stretching step such that the film is stretched less in the second stretching step than in the first stretching step;

laminating the film to at least one substrate web while the film is stretched in the second stretching step to form a laminate; and relaxing the laminate.

14. The process of claim 13, wherein the second stretching step comprises laminating the film to at least one nonwoven web.

15. The process of claim 13, wherein the elastic film comprises an elastic core and at least one skin layer.

16. The process of claim 15, wherein providing the elastic film comprises co-extruding an elastic film having an elastic core and at least two skin layers.

17. The process of claim 13, wherein providing the elastic film, intermittently stretching the film in the first stretching step, relaxing the film after the first stretching step and perforating the film after relaxation are performed by a film manufacturer when intermittently stretching the film in the second stretching step, laminating the film, and relaxing the laminate are performed by an article manufacturer.

18. The process of claim 17, wherein at least a portion of intermittently stretching the film in the second stretching step, laminating the film, or relaxing the laminate involve the use of a cut-and-place apparatus.

19. The process of claim 13, further comprising:

winding the film after perforation; and unwinding the film prior to the second stretching step.

20. The process of claim 13, wherein the film is intermittently stretched in a machine direction using intermeshing gear stretching in the first stretching step and wherein the intermittent stretching in the second stretching step comprises alternately gripping the film with a ribbed roller such that the film is alternately placed under tension in the machine direction and stretched between the ribbed roller and a downstream nip operating at a greater rotation speed as compared to the ribbed roller.

* * * * *